US007524649B2

(12) United States Patent
Ross et al.

(10) Patent No.: US 7,524,649 B2
(45) Date of Patent: Apr. 28, 2009

(54) MODIFIED GROWTH HORMONE FUSION POLYPEPTIDES

(75) Inventors: Richard Ross, Sheffield (GB); Jon Sayers, Sheffield (GB); Peter Artymiuk, Sheffield (GB)

(73) Assignee: Asterion Limited, Sheffield (GB)

( * ) Notice: Subject to any disclaimer, the term of this patent is extended or adjusted under 35 U.S.C. 154(b) by 527 days.

(21) Appl. No.: 10/498,497

(22) PCT Filed: Dec. 6, 2002

(86) PCT No.: PCT/GB02/05523

§ 371 (c)(1),
(2), (4) Date: Jan. 14, 2005

(87) PCT Pub. No.: WO03/070765

PCT Pub. Date: Aug. 28, 2003

(65) Prior Publication Data

US 2005/0123558 A1 Jun. 9, 2005

(30) Foreign Application Priority Data

Dec. 14, 2001 (GB) ................................ 0130052.4

(51) Int. Cl.

| | |
|---|---|
| ***A61K 38/18*** | (2006.01) |
| ***C07K 14/475*** | (2006.01) |
| ***C12N 1/21*** | (2006.01) |
| ***C12N 5/10*** | (2006.01) |
| ***C12N 15/18*** | (2006.01) |
| ***C12N 15/63*** | (2006.01) |

(52) U.S. Cl. ................... 435/69.7; 435/320.1; 435/243; 435/325; 435/70.1; 514/12; 530/350; 530/399

(58) Field of Classification Search ....................... None
See application file for complete search history.

(56) References Cited

U.S. PATENT DOCUMENTS

| | | | | |
|---|---|---|---|---|
| 5,849,535 | A | 12/1998 | Olson et al. | |
| 5,854,026 | A * | 12/1998 | Cunningham et al. ...... | 435/69.4 |
| 2004/0071655 | A1 * | 4/2004 | Ross et al. ................. | 424/85.1 |

FOREIGN PATENT DOCUMENTS

| | | |
|---|---|---|
| WO | WO 97/24445 | 7/1997 |
| WO | WO 01/96565 | 12/2001 |

OTHER PUBLICATIONS

Wilkinson et al. Nature Medicine 13(9): 1108-1113, 2007.*
An article by Wen Y. Chen et al entitled, "In Vitro and in Vivo Studies of Antagonistic Effects of Human Growth Hormone Analogs," The Journal of Biological Chemistry, vol. 269, No. 22, pp. 15592-15897.
An article by Mabrouka Maamra et al entitled, "Studies with a Growth Hormone Antagonist and Dual-Fluorescent Confocal Microscopy Demonstrate that the Full-Length Human Growth Hormone Receptor, but Not the Truncated Isoform, Is Very Rapidly Internalized Independent of Jak2-Stat5 Signaling," The Journal of Biological Chemistry, vol. 274, No, 21, pp. 14791-14798.
An article by R.J.M. Ross et al entitled, "A Short Isoform of the Human Growth Hormone Receptor Functions as a Dominant Negative Inhibitor of the Full-Length Receptor and Generates Large Amounts of Binding Protein," Molecular Endocrinology, pp. 265-273.

* cited by examiner

*Primary Examiner*—Christine J Saoud
(74) *Attorney, Agent, or Firm*—Crowell & Moring LLP

(57) ABSTRACT

The invention relates to chimeric polypeptides wherein said polypeptides comprise a modified binding domain of growth hormone linked to a receptor binding domain of growth hormone receptor; and tandems/oligomers of said modified growth hormone binding domains.

25 Claims, 13 Drawing Sheets

```
start                                6 x His
atggggggtt ctcatcatca tcatcatcat ggtatggcta gcatgactgg
                                                          BamHI
tggacagcaa atgggtcggg atctgtacga cgatgacgat aaggatccaa

ccctTTTCCC AACCATTCCC TTATCCAGGC TTTTTGACAA CGCTAGTCTC
CGCGCCCATC GTCTGCACCA GCTGGCCTTT GACACCTACC AGGAGTTTGA
AGAAGCCTAT ATCCCAAAGG AACAGAAGTA TTCATTCCTG CAGAACCCCC
AGACCTCCCT CTGTTTCTCA GAGTCTATTC CGACACCCTC CAACAGGGAG
GAAACACAAC AGAAATCCAA CCTAGAGCTG CTCCGCATCT CCCTGCTGCT
CATCCAGTCG TGGCTGGAGC CCGTGCAGTT CCTCAGGAGT GTCTTCGCCA
ACAGCCTGGT GTACGGCGCC TCTGACAGCA ACGTCTATGA CCTCCTAAAG
GACCTAGAGG AACGCATCCA AACGCTGATG GGGAGGCTGG AAGATGGCAG
CCCCCGGACT GGGCAGATCT TCAAGCAGAC CTACAGCAAG TTCGACACAA
ACTCACACAA CGATGACGCA CTACTCAAGA ACTACGGGCT GCTCTACTGC
TTCAGGAAGG ACATGGACAA GGTCGAGACA TTCCTGCGCA TCGTGCAGTG
                                    NotI     Stop Stop
CCGCTCTGTG GAGGGCAGCT GTGGCTTCgg cggccgctga taa (SEQ ID NO:1)
```

Figure 5

```
Start                6 x His
atggggggtt ctcatcatca tcatcatcat ggtatggcta gcatgactgg
                                                BamHI
tggacagcaa atgggtcggg atctgtacga cgatgacgat aaggatccaa

ccctTTTCCC AACCATTCCC TTATCCAGGC TTTTTGACAA CGCTAGTCTC
CGCGCCCATC GTCTGCACCA GCTGGCCTTT GACACCTACC AGGAGTTTGA
AGAAGCCTAT ATCCCAAAGG AACAGAAGTA TTCATTCCTG CAGAACCCCC
AGACCTCCCT CTGTTTCTCA GAGTCTATTC CGACACCCTC CAACAGGGAG
GAAACACAAC AGAAATCCAA CCTAGAGCTG CTCCGCATCT CCCTGCTGCT
CATCCAGTCG TGGCTGGAGC CCGTGCAGTT CCTCAGGAGT GTCTTCGCCA
ACAGCCTGGT GTACGGCGCC TCTGACAGCA ACGTCTATGA CCTCCTAAAG
GACCTAGAGG AACGCATCCA AACGCTGATG GGGAGGCTGG AAGATGGCAG
CCCCCGGACT GGGCAGATCT TCAAGCAGAC CTACAGCAAG TTCGACACAA
ACTCACACAA CGATGACGCA CTACTCAAGA ACTACGGGCT GCTCTACTGC
TTCAGGAAGG ACATGGACAA GGTCGAGACA TTCCTGCGCA TCGTGCAGTG
                                   NotI
CCGCTCTGTG GAGGGCAGCT GTGGCTTCGG CGGCCGCGGT GGCGGAGGTA
                                                  EcoRI
GTGGTGGCGG AGGTAGCGGT GGCGGAGGTT CTGGTGGCGG AGGTTCCGAA

TTCGAAATAG TGCAACCAGA TCCACCCATT GCCCTCAACT GGACTTTACT
GAACGTCAGT TTAACTGGGA TTCATGCAGA TATCCAAGTG AGATGGGAAG
CACCACGCAA TGCAGATATT CAGAAAGGAT GGATGGTTCT GGAGTATGAA
CTTCAATACA AAGAAGTAAA TGAAACTAAA TGGAAAATGA TGGACCCTAT
ATTGACAACA TCAGTTCCAG TGTACTCATT GAAAGTGGAT AAGGAATATG
AAGTGCGTGT GAGATCCAAA CAACGAAACT CTGGAAATTA TGGCGAGTTC
AGTGAGGTGC TCTATGTAAC ACTTCCTCAG ATGAGCCAAT TTACATGTGA
              Stop Stop  HindIII
AGAAGATTTC TACtgataaa agctt (SEQ ID NO:2)
```

Figure 6

```
Start                       6 x His
atggggggtt ctcatcatca tcatcatcat ggtatggcta gcatgactgg
                                                        BamHI
tggacagcaa atgggtcggg atctgtacga cgatgacgat aaggatccaa

ccctTTTCCC AACCATTCCC TTATCCAGGC TTTTTGACAA CGCTAGTCTC
CGCGCCCATC GTCTGCACCA GCTGGCCTTT GACACCTACC AGGAGTTTGA
AGAAGCCTAT ATCCCAAAGG AACAGAAGTA TTCATTCCTG CAGAACCCCC
AGACCTCCCT CTGTTTCTCA GAGTCTATTC CGACACCCTC CAACAGGGAG
GAAACACAAC AGAAATCCAA CCTAGAGCTG CTCCGCATCT CCCTGCTGCT
CATCCAGTCG TGGCTGGAGC CCGTGCAGTT CCTCAGGAGT GTCTTCGCCA
ACAGCCTGGT GTACGGCGCC TCTGACAGCA ACGTCTATGA CCTCCTAAAG
GACCTAGAGG AACGCATCCA AACGCTGATG GGGAGGCTGG AAGATGGCAG
CCCCCGGACT GGGCAGATCT TCAAGCAGAC CTACAGCAAG TTCGACACAA
ACTCACACAA CGATGACGCA CTACTCAAGA ACTACGGGCT GCTCTACTGC
TTCAGGAAGG ACATGGACAA GGTCGAGACA TTCCTGCGCA TCGTGCAGTG
                                  NotI
CCGCTCTGTG GAGGGCAGCT GTGGCTTCGG CGGCCGCGGT GGCGGAGGTA
                                                  EcoRI
GTGGTGGCGG AGGTAGCGGT GGCGGAGGTT CTGGTGGCGG AGGTTCCGAA

TTCTTTTCTG GAAGTGAGGC CACAGCAGCT ATCCTTAGCA GAGCACCCTG
GAGTCTGCAA AGTGTTAATC CAGGCCTAAA GACAAATTCT TCTAAGGAGC
CTAAATTCAC CAAGTGCCGT TCACCTGAGC GAGAGACTTT TTCATGCCAC
TGGACAGATG AGGTTCATCA TGGTACAAAG AACCTAGGAC CCATACAGCT
GTTCTATACC AGAAGGAACA CTCAAGAATG GACTCAAGAA TGGAAAGAAT
GCCCTGATTA TGTTTCTGCT GGGGAAAACA GCTGTTACTT TAATTCATCG
TTTACCTCCA TCTGGATACC TTATTGTATC AAGCTAACTA GCAATGGTGG
TACAGTGGAT GAAAAGTGTT TCTCTGTTGA TGAAATAGTG CAACCAGATC
CACCCATTGC CCTCAACTGG ACTTTACTGA ACGTCAGTTT AACTGGGATT
CATGCAGATA TCCAAGTGAG ATGGGAAGCA CCACGCAATG CAGATATTCA
GAAAGGATGG ATGGTTCTGG AGTATGAACT TCAATACAAA GAAGTAAATG
AAACTAAATG GAAAATGATG GACCCTATAT TGACAACATC AGTTCCAGTG
TACTCATTGA AAGTGGATAA GGAATATGAA GTGCGTGTGA GATCCAAACA
ACGAAACTCT GGAAATTATG GCGAGTTCAG TGAGGTGCTC TATGTAACAC
                                             Stop Stop
HindIII
TTCCTCAGAT GAGCCAATTT ACATGTGAA GAAGATTTCTA Ctgataaaag

ctt (SEQ ID NO:3)
```

Figure 7

```
Start                                6 x His
atggggggtt ctcatcatca tcatcatcat ggtatggcta gcatgactgg
                                                         BamHI
tggacagcaa atgggtcggg atctgtacga cgatgacgat aaggatccaa

ccctTTTCCC AACCATTCCC TTATCCAGGC TTTTTGACAA CGCTAGTCTC
CGCGCCCATC GTCTGCACCA GCTGGCCTTT GACACCTACC AGGAGTTTGA
AGAAGCCTAT ATCCCAAAGG AACAGAAGTA TTCATTCCTG CAGAACCCCC
AGACCTCCCT CTGTTTCTCA GAGTCTATTC CGACACCCTC CAACAGGGAG
GAAACACAAC AGAAATCCAA CCTAGAGCTG CTCCGCATCT CCCTGCTGCT
CATCCAGTCG TGGCTGGAGC CCGTGCAGTT CCTCAGGAGT GTCTTCGCCA
ACAGCCTGGT GTACGGCGCC TCTGACAGCA ACGTCTATGA CCTCCTAAAG
GACCTAGAGG AACGCATCCA AACGCTGATG GGGAGGCTGG AAGATGGCAG
CCCCCGGACT GGGCAGATCT TCAAGCAGAC CTACAGCAAG TTCGACACAA
ACTCACACAA CGATGACGCA CTACTCAAGA ACTACGGGCT GCTCTACTGC
TTCAGGAAGG ACATGGACAA GGTCGAGACA TTCCTGCGCA TCGTGCAGTG
                                    NotI
CCGCTCTGTG GAGGGCAGCT GTGGCTTCGG CGGCCGCGGT GGCGGAGGTA
                                                      EcoRI
GTGGTGGCGG AGGTAGCGGT GGCGGAGGTT CTGGTGGCGG AGGTTCCGAA

TTCTTTCCCG AAGTGAGGCC ACAGCAGCTA TCCTTAGCAG AGCACCCTGA
ACCATTCCCT TATCCAGGCT TTTTGACAAC GCTAGTCTCC GCGCCCATCG
TCTGCACCAG CTGGCCTTTG ACACCTACCA GGAGTTTGAA GAAGCCTATA
TCCCAAAGGA ACAGAAGTAT TCATTCCTGC AGAACCCCCA GACCTCCCTC
TGTTTCTCAG AGTCTATTCC GACACCCTCC AACAGGGAGG AAACACAACA
GAAATCCAAC CTAGAGCTGC TCCGCATCTC CCTGCTGCTC ATCCAGTCGT
GGCTGGAGCC CGTGCAGTTC CTCAGGAGTG TCTTCGCCAA CAGCCTGGTG
TACGGCGCCT CTGACAGCAA CGTCTATGAC CTCCTAAAGG ACCTAGAGGA
ACGCATCCAA ACGCTGATGG GGAGGCTGGA AGATGGCAGC CCCCGGACTG
GGCAGATCTT CAAGCAGACC TACAGCAAGT TCGACACAAA CTCACACAAC
GATGACGCAC TACTCAAGAA CTACGGGCTG CTCTACTGCT TCAGGAAGGA
CATGGACAAG GTCGAGACAT TCCTGCGCAT CGTGCAGTGC CGCTCTGTGG
                      Stop  Stop  HindIII
AGGGCAGCTG TGGCTTCtga taaaagctt (SEQ ID NO:4)
```

Figure 8

| | | | | | | | | | | | | | | | |
|---|---|---|---|---|---|---|---|---|---|---|---|---|---|---|---|
| 1 | Phe | Pro | Thr | Ile | Pro | Leu | Ser | Arg | Leu | Phe | Asp | Asn | Ala | Ser | Leu |
| 16 | Arg | Ala | His | Arg | Leu | His | Gln | Leu | Ala | Phe | Asp | Thr | Tyr | Gln | Glu |
| 31 | Phe | Glu | Glu | Ala | Tyr | Ile | Pro | Lys | Glu | Gln | Lys | Tyr | Ser | Phe | Leu |
| 46 | Gln | Asn | Pro | Gln | Thr | Ser | Leu | Cys | Phe | Ser | Glu | Ser | Ile | Pro | Thr |
| 61 | Pro | Ser | Asn | Arg | Glu | Glu | Thr | Gln | Gln | Lys | Ser | Asn | Leu | Glu | Leu |
| 76 | Leu | Arg | Ile | Ser | Leu | Leu | Leu | Ile | Gln | Ser | Trp | Leu | Glu | Pro | Val |
| 91 | Gln | Phe | Leu | Arg | Ser | Val | Phe | Ala | Asn | Ser | Leu | Val | Tyr | Gly | Ala |
| 106 | Ser | Asp | Ser | Asn | Val | Tyr | Asp | Leu | Leu | Lys | Asp | Leu | Glu | Glu | Gly |
| 121 | Ile | Gln | Thr | Leu | Met | Gly | Arg | Leu | Glu | Asp | Gly | Ser | Pro | Arg | Thr |
| 136 | Gly | Gln | Ile | Phe | Lys | Gln | Thr | Tyr | Ser | Lys | Phe | Asp | Thr | Asn | Ser |
| 151 | His | Asn | Asp | Asp | Ala | Leu | Leu | Lys | Asn | Tyr | Gly | Leu | Leu | Tyr | Cys |
| 166 | Phe | Arg | Lys | Asp | Met | Asp | Lys | Val | Glu | Thr | Phe | Leu | Arg | Ile | Val |
| 181 | Gln | Cys | Arg | Ser | Val | Glu | Gly | Ser | Cys | Gly | Phe | (SEQ ID NO:5) | | | |

Figure 12

| | | | | | | | | | | | | | | | |
|---|---|---|---|---|---|---|---|---|---|---|---|---|---|---|---|
| 1 | TTC | CCA | ACC | ATT | CCC | TTA | TCC | AGG | CTT | TTT | GAC | AAC | GCT | AGT | CTC |
| 46 | CGC | GCC | CAT | CGT | CTG | CAC | CAG | CTG | GCC | TTT | GAC | ACC | TAC | CAG | GAG |
| 91 | TTT | GAA | GAA | GCC | TAT | ATC | CCA | AAG | GAA | CAG | AAG | TAT | TCA | TTC | CTG |
| 136 | CAG | AAC | CCC | CAG | ACC | TCC | CTC | TGT | TTC | TCA | GAG | TCT | ATT | CCG | ACA |
| 181 | CCC | TCC | AAC | AGG | GAG | GAA | ACA | CAA | CAG | AAA | TCC | AAC | CTA | GAG | CTG |
| 226 | CTC | CGC | ATC | TCC | CTG | CTG | CTC | ATC | CAG | TCG | TGG | CTG | GAG | CCC | GTG |
| 271 | CAG | TTC | CTC | AGG | AGT | GTC | TTC | GCC | AAC | AGC | CTG | GTG | TAC | GGC | GCC |
| 316 | TCT | GAC | AGC | AAC | GTC | TAT | GAC | CTC | CTA | AAG | GAC | CTA | GAG | GAA | GGC |
| 361 | ATC | CAA | ACG | CTG | ATG | GGG | AGG | CTG | GAA | GAT | GGC | AGC | CCC | CGG | ACT |
| 406 | GGG | CAG | ATC | TTC | AAG | CAG | ACC | TAC | AGC | AAG | TTC | GAC | ACA | AAC | TCA |
| 451 | CAC | AAC | GAT | GAC | GCA | CTA | CTC | AAG | AAC | TAC | GGG | CTG | CTC | TAC | TGC |
| 496 | TTC | AGG | AAG | GAC | ATG | GAC | AAG | GTC | GAG | ACA | TTC | CTG | CGC | ATC | GTG |
| 541 | CAG | TGC | CGC | TCT | GTG | GAG | GGC | AGC | TGT | GGC | TTC | (SEQ ID NO:6) | | | |

Figure 13

SEQUENCE LISTING

```
<160> NUMBER OF SEQ ID NOS: 6

<210> SEQ ID NO 1
<211> LENGTH: 693
<212> TYPE: DNA
<213> ORGANISM: Homo sapien

<400> SEQUENCE: 1

atgggggggtt ctcatcatca tcatcatcat ggtatggcta gcatgactgg tggacagcaa      60

atgggtcggg atctgtacga cgatgacgat aaggatccaa cccttttccc aaccattccc     120

ttatccaggc tttttgacaa cgctagtctc cgcgcccatc gtctgcacca gctggccttt     180

gacacctacc aggagtttga agaagcctat atcccaaagg aacagaagta ttcattcctg     240

cagaaccccc agacctccct ctgtttctca gagtctattc cgacaccctc caacagggag     300

gaaacacaac agaaatccaa cctagagctg ctccgcatct ccctgctgct catccagtcg     360
```

-continued

```
tggctggagc ccgtgcagtt cctcaggagt gtcttcgcca acagcctggt gtacggcgcc    420

tctgacagca acgtctatga cctcctaaag gacctagagg aacgcatcca aacgctgatg    480

gggaggctgg aagatggcag cccccggact gggcagatct tcaagcagac ctacagcaag    540

ttcgacacaa actcacacaa cgatgacgca ctactcaaga actacgggct gctctactgc    600

ttcaggaagg acatggacaa ggtcgagaca ttcctgcgca tcgtgcagtg ccgctctgtg    660

gagggcagct gtggcttcgg cggccgctga taa                                 693
```

<210> SEQ ID NO 2
<211> LENGTH: 1125
<212> TYPE: DNA
<213> ORGANISM: Homo sapien

<400> SEQUENCE: 2

```
atggggggtt ctcatcatca tcatcatcat ggtatggcta gcatgactgg tggacagcaa     60

atgggtcggg atctgtacga cgatgacgat aaggatccaa ccctttttccc aaccattccc   120

ttatccaggc tttttgacaa cgctagtctc cgcgcccatc gtctgcacca gctggccttt    180

gacacctacc aggagtttga agaagcctat atcccaaagg aacagaagta ttcattcctg    240

cagaaccccc agacctccct ctgtttctca gagtctattc cgacaccctc caacagggag    300

gaaacacaac agaaatccaa cctagagctg ctccgcatct ccctgctgct catccagtcg    360

tggctggagc ccgtgcagtt cctcaggagt gtcttcgcca acagcctggt gtacggcgcc    420

tctgacagca acgtctatga cctcctaaag gacctagagg aacgcatcca aacgctgatg    480

gggaggctgg aagatggcag cccccggact gggcagatct tcaagcagac ctacagcaag    540

ttcgacacaa actcacacaa cgatgacgca ctactcaaga actacgggct gctctactgc    600

ttcaggaagg acatggacaa ggtcgagaca ttcctgcgca tcgtgcagtg ccgctctgtg    660

gagggcagct gtggcttcgg cggccgcggt ggcggaggta gtggtggcgg aggtagcggt    720

ggcggaggtt ctggtggcgg aggttccgaa ttcgaaatag tgcaaccaga tccacccatt    780

gccctcaact ggactttact gaacgtcagt ttaactggga ttcatgcaga tatccaagtg    840

agatgggaag caccacgcaa tgcagatatt cagaaaggat ggatggttct ggagtatgaa    900

cttcaataca aagaagtaaa tgaaactaaa tggaaaatga tggaccctat attgacaaca    960

tcagttccag tgtactcatt gaaagtggat aaggaatatg aagtgcgtgt gagatccaaa   1020

caacgaaact ctggaaatta tggcgagttc agtgaggtgc tctatgtaac acttcctcag   1080

atgagccaat ttacatgtga agaagatttc tactgataaa agctt                   1125
```

<210> SEQ ID NO 3
<211> LENGTH: 1503
<212> TYPE: DNA
<213> ORGANISM: Homo sapien

<400> SEQUENCE: 3

```
atggggggtt ctcatcatca tcatcatcat ggtatggcta gcatgactgg tggacagcaa     60

atgggtcggg atctgtacga cgatgacgat aaggatccaa ccctttttccc aaccattccc   120

ttatccaggc tttttgacaa cgctagtctc cgcgcccatc gtctgcacca gctggccttt    180

gacacctacc aggagtttga agaagcctat atcccaaagg aacagaagta ttcattcctg    240

cagaaccccc agacctccct ctgtttctca gagtctattc cgacaccctc caacagggag    300

gaaacacaac agaaatccaa cctagagctg ctccgcatct ccctgctgct catccagtcg    360
```

-continued

```
tggctggagc ccgtgcagtt cctcaggagt gtcttcgcca acagcctggt gtacggcgcc    420

tctgacagca acgtctatga cctcctaaag gacctagagg aacgcatcca aacgctgatg    480

gggaggctgg aagatggcag cccccggact gggcagatct tcaagcagac ctacagcaag    540

ttcgacacaa actcacacaa cgatgacgca ctactcaaga actacgggct gctctactgc    600

ttcaggaagg acatggacaa ggtcgagaca ttcctgcgca tcgtgcagtg ccgctctgtg    660

gagggcagct gtggcttcgg cggccgcggt ggcggaggta gtggtggcgg aggtagcggt    720

ggcggaggtt ctggtggcgg aggttccgaa ttcttttctg gaagtgaggc cacagcagct    780

atccttagca gagcaccctg gagtctgcaa agtgttaatc caggcctaaa gacaaattct    840

tctaaggagc ctaaattcac caagtgccgt tcacctgagc gagagacttt ttcatgccac    900

tggacagatg aggttcatca tggtacaaag aacctaggac ccatacagct gttctatacc    960

agaaggaaca ctcaagaatg gactcaagaa tggaaagaat gccctgatta tgtttctgct   1020

ggggaaaaca gctgttactt taattcatcg tttacctcca tctggatacc ttattgtatc   1080

aagctaacta gcaatggtgg tacagtggat gaaaagtgtt tctctgttga tgaaatagtg   1140

caaccagatc cacccattgc cctcaactgg actttactga acgtcagttt aactgggatt   1200

catgcagata tccaagtgag atgggaagca ccacgcaatg cagatattca gaaaggatgg   1260

atggttctgg agtatgaact tcaatacaaa gaagtaaatg aaactaaatg gaaaatgatg   1320

gaccctatat tgacaacatc agttccagtg tactcattga aagtggataa ggaatatgaa   1380

gtgcgtgtga gatccaaaca acgaaactct ggaaattatg gcgagttcag tgaggtgctc   1440

tatgtaacac ttcctcagat gagccaattt acatgtgaag aagatttcta ctgataaaag   1500

ctt                                                                 1503
```

<210> SEQ ID NO 4
<211> LENGTH: 1379
<212> TYPE: DNA
<213> ORGANISM: Homo sapien

<400> SEQUENCE: 4

```
atggggggtt ctcatcatca tcatcatcat ggtatggcta gcatgactgg tggacagcaa     60

atgggtcggg atctgtacga cgatgacgat aaggatccaa ccctttttccc aaccattccc    120

ttatccaggc tttttgacaa cgctagtctc cgcgcccatc gtctgcacca gctggccttt    180

gacacctacc aggagtttga agaagcctat atcccaaagg aacagaagta ttcattcctg    240

cagaaccccc agacctccct ctgtttctca gagtctattc cgacaccctc caacagggag    300

gaaacacaac agaaatccaa cctagagctg ctccgcatct ccctgctgct catccagtcg    360

tggctggagc ccgtgcagtt cctcaggagt gtcttcgcca acagcctggt gtacggcgcc    420

tctgacagca acgtctatga cctcctaaag gacctagagg aacgcatcca aacgctgatg    480

gggaggctgg aagatggcag cccccggact gggcagatct tcaagcagac ctacagcaag    540

ttcgacacaa actcacacaa cgatgacgca ctactcaaga actacgggct gctctactgc    600

ttcaggaagg acatggacaa ggtcgagaca ttcctgcgca tcgtgcagtg ccgctctgtg    660

gagggcagct gtggcttcgg cggccgcggt ggcggaggta gtggtggcgg aggtagcggt    720

ggcggaggtt ctggtggcgg aggttccgaa ttctttcccg aagtgaggcc acagcagcta    780

tccttagcag agcaccctga accattccct tatccaggct tttgacaac gctagtctcc    840

gcgcccatcg tctgcaccag ctggcctttg acacctacca ggagtttgaa gaagcctata    900

tcccaaagga acagaagtat tcattcctgc agaaccccca gacctccctc tgtttctcag    960
```

-continued

```
agtctattcc gacaccctcc aacagggagg aaacacaaca gaaatccaac ctagagctgc   1020

tccgcatctc cctgctgctc atccagtcgt ggctggagcc cgtgcagttc ctcaggagtg   1080

tcttcgccaa cagcctggtg tacggcgcct ctgacagcaa cgtctatgac ctcctaaagg   1140

acctagagga acgcatccaa acgctgatgg ggaggctgga agatggcagc cccggactg    1200

ggcagatctt caagcagacc tacagcaagt tcgacacaaa ctcacacaac gatgacgcac   1260

tactcaagaa ctacgggctg ctctactgct tcaggaagga catggacaag gtcgagacat   1320

tcctgcgcat cgtgcagtgc cgctctgtgg agggcagctg tggcttctga taaaagctt    1379
```

```
<210> SEQ ID NO 5
<211> LENGTH: 191
<212> TYPE: PRT
<213> ORGANISM: Homo sapien

<400> SEQUENCE: 5

Phe Pro Thr Ile Pro Leu Ser Arg Leu Phe Asp Asn Ala Ser Leu Arg
1               5                   10                  15

Ala His Arg Leu His Gln Leu Ala Phe Asp Thr Tyr Gln Glu Phe Glu
            20                  25                  30

Glu Ala Tyr Ile Pro Lys Glu Gln Lys Tyr Ser Phe Leu Gln Asn Pro
        35                  40                  45

Gln Thr Ser Leu Cys Phe Ser Glu Ser Ile Pro Thr Pro Ser Asn Arg
    50                  55                  60

Glu Glu Thr Gln Gln Lys Ser Asn Leu Glu Leu Leu Arg Ile Ser Leu
65                  70                  75                  80

Leu Leu Ile Gln Ser Trp Leu Glu Pro Val Gln Phe Leu Arg Ser Val
                85                  90                  95

Phe Ala Asn Ser Leu Val Tyr Gly Ala Ser Asp Ser Asn Val Tyr Asp
            100                 105                 110

Leu Leu Lys Asp Leu Glu Glu Gly Ile Gln Thr Leu Met Gly Arg Leu
        115                 120                 125

Glu Asp Gly Ser Pro Arg Thr Gly Gln Ile Phe Lys Gln Thr Tyr Ser
    130                 135                 140

Lys Phe Asp Thr Asn Ser His Asn Asp Asp Ala Leu Leu Lys Asn Tyr
145                 150                 155                 160

Gly Leu Leu Tyr Cys Phe Arg Lys Asp Met Asp Lys Val Glu Thr Phe
                165                 170                 175

Leu Arg Ile Val Gln Cys Arg Ser Val Glu Gly Ser Cys Gly Phe
            180                 185                 190
```

```
<210> SEQ ID NO 6
<211> LENGTH: 573
<212> TYPE: DNA
<213> ORGANISM: Homo sapien

<400> SEQUENCE: 6

ttcccaacca ttcccttatc caggcttttt gacaacgcta gtctccgcgc ccatcgtctg     60

caccagctgg cctttgacac ctaccaggag tttgaagaag cctatatccc aaaggaacag    120

aagtattcat tcctgcagaa cccccagacc tccctctgtt tctcagagtc tattccgaca    180

ccctccaaca gggaggaaac acaacagaaa tccaacctag agctgctccg catctccctg    240

ctgctcatcc agtcgtggct ggagcccgtg cagttcctca ggagtgtctt cgccaacagc    300

ctggtgtacg gcgcctctga cagcaacgtc tatgacctcc taaaggacct agaggaaggc    360
```

-continued

| | |
|---|---|
| atccaaacgc tgatggggag gctggaagat ggcagccccc ggactgggca gatcttcaag | 420 |
| cagacctaca gcaagttcga cacaaactca cacaacgatg acgcactact caagaactac | 480 |
| gggctgctct actgcttcag gaaggacatg gacaaggtcg agacattcct gcgcatcgtg | 540 |
| cagtgccgct ctgtggaggg cagctgtggc ttc | 573 |

MODIFIED GROWTH HORMONE FUSION POLYPEPTIDES

The invention relates to chimeric polypeptides wherein said polypeptides comprise a modified binding domain of growth hormone linked to a receptor binding domain of growth hormone receptor; and tandems/oligomers of said modified growth hormone binding domains.

BACKGROUND OF THE INVENTION

GH is a member of a large family of hormones involved in the regulation of mammalian growth and development. Human GH is a 22 kDa polypeptide which is involved in a number of biological processes. For example, cell growth, lactation, the activation of macrophages and the regulation of energy metabolism. GH interacts sequentially with two membrane bound GHR's via two separate sites on GH referred as site 1 and site 2. Site 1 is a high affinity binding site and site 2 a low affinity site. A single GH molecule binds 1 GHR via site 1. A second GHR is then recruited via site 2 to form a GHR:GH:GHR complex. The complex is then internalised and activates a signal transduction cascade leading to changes in gene expression.

The extracellular domain of the GHR exists as two linked domains each of approximately 100 amino acids (SD-100), the C-terminal SD-100 domain (b) being closest to the cell surface and the N-terminal SD-100 domain (a) being furthest away. It is a conformational change in these two domains that occurs on hormone binding with the formation of the trimeric complex GHR-GH-GHR.

Modified GH's are disclosed in U.S. Pat. No. 5,849,535 which is incorporated by reference. The modification to GH is at both site 1 and site 2 binding sites. The modifications to site 1 produce a GH molecule which has a higher affinity for GHR compared to wild-type GH. These modified GH molecules act agonists. There is also disclosure of site 2 modifications which result in the creation of GH antagonists. Further examples of modifications to GH which alter the binding affinity of GH for site 1 are disclosed in U.S. Pat. Nos. 5,854,026; 6,004,931; 6,022,711; 6,057,292; and 6,136,563 each of which are incorporated by reference. A summary of the modifications made to site 1 is provided in Table 1. Modifications to site 2 are also disclosed, in particular amino acid residue G120 which when modified to either arginine, lysine, tryptophan, tyrosine, phenylalanine, or glutamic acid creates a GH molecule with antagonistic properties.

In addition, the modified GH is coated in polyethylene glycol (PEG) by a process known as "pegylation" this has several beneficial effects. Firstly, the PEG coat increases the effective molecular weight of GH from 22 kD to approximately 40 kD. The effect this has is to decrease glomerular filtration of GH thereby increasing the half-life of GH in vivo which reduces the dose administered to produce the desired effect. In addition pegylation is thought to reduce both the immunogenicity and toxicity of proteins which are treated in this way, see Abuchowski et al J Biol Chem., 252, 3578-3581, (1977).

However, a consequence of pegylation is to reduce the affinity of the modified GH molecule for GHR. This means that an increased dose is required to counter the reduced affinity. This is undesirable since it counteracts the advantageous effect of pegylation with respect to increasing the half life of modified GH. It would be desirable to provide a modified GH molecule which does not require pegylation but has an increased half-life and also has the added benefits of reduced immunogenicity and lacks toxicity.

DESCRIPTION OF THE INVENTION

According to a first aspect of the invention there is provided a chimeric polypeptide comprising:

i) at least one modified binding domain of growth hormone wherein said modification is the addition, deletion or substitution of at least one amino acid residue; and ii) a growth hormone binding domain of a growth hormone receptor.

In a preferred embodiment of the invention said polypeptide is modified in the site 1 binding domain of growth hormone.

In a further preferred embodiment of the invention said polypeptide is modified in the site 2 binding domain of growth hormone.

In a yet further preferred embodiment of the invention said polypeptide is modified at both site 1 and site 2 of growth hormone.

As previously described, site 1 mutations are known in the art which increase the affinity of growth hormone for its binding domain on growth hormone receptor. Such modified growth hormone acts as an agonist. If a site 1 modification is combined with a site 2 modification wherein the latter modification results in an inactive or partially active site 2 binding site then such a molecule is an antagonist. A modification just to site 2 which exploits a wild-type site 1 binding site also creates an antagonist.

In a further preferred embodiment of the invention there is provided a polypeptide comprising a site 1 binding domain which has been modified by amino acid substitution wherein said modification is selected from the group consisting of: histidine 18 with alanine or aspartic acid; and/or histidine 21 with asparagine; and/or glutamine 22 with alanine; and/or phenylalanine 25 with alanine; and/or aspartic acid 26 with alanine; and/or glutamine 29 with alanine; and/or glutamic acid 167 with alanine; and/or aspartic acid 171 with serine; and/or lysine 172 with serine or alanine; and/or isoleucine 179 with tyrosine, of the sequence represented in FIG. 13.

Preferably said modification to increase the affinity of site 1 for its binding domain in GHR consists of the amino acid substitutions: histidine 18 aspartic acid; histidine 21 asparagine; arginine 167 asparagine; aspartic acid 171 arginine; glutamic acid 174 serine; and isoleucine 179 threonine; as represented by the GH amino acid sequence in FIG. 13.

In a further preferred embodiment of the invention said modification to increase the affinity of site 1 for its binding domain in GHR consists of the amino acid substitutions: histidine 18 alanine; glutamine 22 alanine; phenylalanine 25 alanine; aspartic acid 26 alanine; glutamine 29 alanine; glutamic acid 65 alanine; lysine 168 alanine; and glutamic acid 174 alanine; as represented by the GH amino acid sequence in FIG. 13.

In a further preferred embodiment of the invention said site 2 modification is to amino acid residue 120 of the sequence presented in FIG. 13. Preferably said site 2 modification is combined with site 1 modifications as herein disclosed. Alternatively, GH is modified only at amino acid residue glycine 120.

In a preferred embodiment of the invention said site 2 modification is a substitution of glycine for an amino acid selected from the group consisting of: arginine; alanine; lysine; tryptophan; tyrosine; phenylalanine; and glutamic acid. Preferably said substitution is glycine 120 for arginine or lysine or alanine.

In a further preferred embodiment of the invention the growth hormone binding domain of GHR is the extracellular domain of GHR. More preferably the binding domain is the C-terminal SD-100 domain of GH.

Alternatively said binding domain is the full length GHR.

In a preferred embodiment of the invention said chimeric polypeptide is a fusion protein wherein the modified GH is an inframe translational fusion with GHR, or part thereof. Preferably, said fusion polypeptide comprises modified GH and the C-terminal SD-100 domain of GHR.

In an alternative further preferred embodiment of the invention, the modified binding domain of GH is linked by a linker to the GH binding domain of GHR. The linker may be flexible.

The linker could be at any residue within the extracellular domain of the receptor which would allow the modified GH to flexibly bind with the free receptor at the cell surface. Preferably the linkage is made between a residue close to the C-terminus of the modified GH molecule and a residue close to the N-terminus of GHR. More preferably the linkage is made between a residue close to the C-terminus of modified GH molecule and a residue close to the N-terminal of the N-terminal of the C-terminal SD-100. More preferably the linkage is made at any of residues 126-128 of the N-terminus of the C-terminal SD-100 of the GHR. In one embodiment of the invention, the linkage is made at residue 127 of the N-terminus of the C-terminal SD-100. Preferably the linker is a peptide.

The crystal structure of the GHR:GH:GHR complex reveals that the distance between the C-terminus of GH (residue 191) and N-terminus of the C-terminus SD-100 (residue 126-128) is 10A. This provides invaluable information with respect to linker design.

Preferably the linker is a polypeptide which comprises 5 to 30 amino acid residues. More preferably the linker comprises 10 to 20 amino acid residues. More preferably still the linker comprises at least one copy of the peptide: Gly Gly Gly Gly Ser (SEQ ID NO:7) (hereinafter referred to as "Gly4Ser").

In one embodiment of the invention the linker is 10 amino acids in length and comprises two copies of the Gly4Ser linker. In an alternative embodiment of the invention, the linker is 15 amino acids in length and comprises three copies of the Gly4Ser linker. In yet an alternative embodiment, the linker is 20 amino acids in length and comprises four copies of the Gly4Ser linker.

In a preferred embodiment of the invention said polypeptide is derived from human GH and human GHR.

According to a further aspect of the invention there is provided a nucleic acid molecule which encodes a polypeptide according to the invention selected from the group consisting of:

i) a nucleic acid molecule as represented by the nucleic acid sequence in FIG. 13; and ii) a nucleic acid molecule which hybridises to the nucleic acid sequence in (i).

Nucleic acid molecules which encode a modified growth hormone according to the invention can typically be synthesized by molecular techniques known in the art and include recombinant methods as well as the synthesis of nucleic acid molecules using oligonucleotide synthesizers.

In a preferred embodiment of the invention said nucleic acid molecule hybridises under stringent hybridisation.

The term "stringent hybridisation conditions" as used herein refers to parameters with which the art is familiar. Nucleic acid hybridization parameters may be found in references which compile such methods, e.g. *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. More specifically, stringent conditions, as used herein, refers, for example, to hybridization at 65° C. in hybridization buffer (3.5×SSC, 0.02% Ficoll, 0.02% polyvinyl pyrrolidone, 0.02% Bovine Serum Albumin, 2.5 mM $NaH_2PO_4$(pH7), 0.5% SDS, 2 mM EDTA). SSC is 0.15M sodium chloride/0.015M sodium citrate, pH7; SDS is sodium dodecyl sulphate; and EDTA is ethylenediaminetetracetic acid. After hybridization, the membrane upon which the DNA is transferred is washed at 2×SSC at room temperature and then at 0.1-0.5×SSC/0.1×SDS at temperatures up to 68° C.

According to a further aspect of the invention there is provided a vector comprising the nucleic acid molecule according to the invention.

In a preferred embodiment of the invention said vector is an expression vector adapted for recombinant gene expression.

Typically said adaptation includes, by example and not by way of limitation, the provision of transcription control sequences (promoter sequences) which mediate cell/tissue specific expression. These promoter sequences may be cell/tissue specific, inducible or constitutive.

Promoter is an art-recognised term and, for the sake of clarity, includes the following features which are provided by example only, and not by way of limitation. Enhancer elements are cis acting nucleic acid sequences often found 5' to the transcription initiation site of a gene (enhancers can also be found 3' to a gene sequence or even located in intronic sequences and is therefore position independent). Enhancers function to increase the rate of transcription of the gene to which the enhancer is linked. Enhancer activity is responsive to trans acting transcription factor which have been shown to bind specifically to enhancer elements. The binding/activity of transcription factors (please see Eukaryotic Transcription Factors, by David S Latchman, Academic Press Ltd, San Diego) is responsive to a number of environmental cues which include, by example and not by way of limitation, intermediary metabolites and/or environmental effectors.

Promoter elements also include so called TATA box and RNA polymerase initiation selection (RIS) sequences which function to select a site of transcription initiation.

These sequences also bind polypeptides which function, inter alia, to facilitate transcription initiation selection by RNA polymerase.

Adaptations also include the provision of selectable markers and autonomous replication sequences which both facilitate the maintenance of said vector in either the eukaryotic cell or prokaryotic host. Vectors which are maintained autonomously are referred to as episomal vectors. Episomal vectors are desirable since these molecules can incorporate large DNA fragments (30-50 kb DNA). Episomal vectors of this type are described in WO98/07876 which is incorporated by reference.

Adaptations which facilitate the expression of vector encoded genes include the provision of transcription termination/polyadenylation sequences. This also includes the provision of internal ribosome entry sites (IRES) which function to maximise expression of vector encoded genes arranged in bicistronic or multi-cistronic expression cassettes.

These adaptations are well known in the art. There is a significant amount of published literature with respect to expression vector construction and recombinant DNA techniques in general. Please see, Sambrook et al (1989) Molecular Cloning: A Laboratory Manual, Cold Spring Harbour Laboratory, Cold Spring Harbour, N.Y. and references therein; Marston, F (1987) DNA Cloning Techniques: A Practical Approach Vol III IRL Press, Oxford UK; DNA Cloning:

F M Ausubel et al, Current Protocols in Molecular Biology, John Wiley & Sons, Inc. (1994).

According to a further aspect of the invention there is provided the use of the polypeptide according to the invention as a pharmaceutical. In a preferred embodiment of the invention said polypeptide is for use in the manufacture of a medicament for the treatment of a condition selected from the group consisting of: gigantism, acromegaly; cancer (e.g. Wilm's tumour, osteogenic sarcoma, breast, colon, prostate, thyroid); diabetic retinopathy; diabetic nephropathy and other complications of diabetes and GH excess.

The polypeptides and compositions of the invention can be administered by any conventional route, including injection or by gradual infusion over time. The administration may, for example, be oral, intravenous, intraperitoneal, intramuscular, intracavity, intraocular, subcutaneous, or transdermal. The pharmaceutical compositions may conveniently be presented in unit dosage form and may be prepared by any of the methods well-known in the art of pharmacy.

When administered, the pharmaceutical preparations of the invention are applied in pharmaceutically-acceptable amounts and in pharmaceutically-acceptable compositions. The term "pharmaceutically acceptable" means a non-toxic material that does not interfere with the effectiveness of the biological activity of the active ingredients. Such preparations may routinely contain salts, buffering agents, preservatives, compatible carriers, and optionally other therapeutic agents.

The compositions may be combined, if desired, with a pharmaceutically-acceptable carrier. The term "pharmaceutically-acceptable carrier" means one or more compatible solid or liquid fillers, diluents or encapsulating substances which are suitable for administration into a human. The term "carrier" denotes an organic or inorganic ingredient, natural or synthetic, with which the active ingredient is combined to facilitate the application. The pharmaceutical compositions may contain suitable buffering agents, including: acetic acid in a salt; citric acid in a salt; boric acid in a salt; and phosphoric acid in a salt. The pharmaceutical compositions also may contain, optionally, suitable preservatives, such as: benzalkonium chloride; chlorobutanol; parabens and thimerosal.

According to a yet further aspect of the invention there is provided a cell transformed or transfected with the nucleic acid or vector according to the invention.

In a preferred embodiment of the invention said cell is a eukaryotic cell. Preferably said cell is selected from the group consisting of: a slime mould (e.g. *Dictyostelium* spp) a yeast cell (e.g. *Saccharomyces cerevisae; Pichia* spp); a mammalian cell (e.g. Chinese Hamster Ovary); a plant cell; an insect cell (e.g.*Spodoptera* spp).

In an alternative preferred embodiment said cell is a prokaryotic cell, preferably *Escherichia coli* or *Bacillus* spp.

According to a further aspect of the invention there is provided a method to manufacture the polypeptide according to the invention comprising:

i) providing a cell according to the invention;

ii) incubating said cell under conditions conducive to the production of the polypeptide according to the invention; and optionally iii) isolating the polypeptide from the cell or the cell culture medium.

In a preferred method of the invention said polypeptide is provided with a secretion signal to facilitate the purification of the polypeptide from said cell. More preferably still said polypeptide is provided with an affinity tag to facilitate the purification of the polypeptide from said cell or the cell culture medium.

According to a yet further aspect of the invention there is provided a method of treatment of a mammal, preferably a human, comprising administering to said mammal the polypeptide according to the invention.

According to a further aspect of the invention there is provided a chimeric polypeptide comprising more than two modified growth hormone binding domains wherein said modification is the addition, deletion or substitution of at least one amino acid residue.

In a preferred embodiment of the invention there is provided a chimeric polypeptide comprising a plurality of modified growth hormone binding domains.

In a further preferred embodiment of the invention there is provided a chimeric polypeptide comprising at least two modified site 2 growth hormone binding domains.

In a further preferred embodiment of the invention there is provided a chimeric polypeptide comprising 3, 4, 5, 6, 7, 8, 9, 10 modified site 2 growth hormone binding domains.

In a yet further preferred embodiment of the invention said chimeric polypeptide comprises more than two modified growth hormone binding domains linked together by a linker molecule. Preferably said linker molecule is as hereinbefore disclosed.

According to a yet further aspect of the invention said chimeric polypeptide comprising more than two modified growth hormone binding domains further comprises at least one growth hormone binding domain of a growth hormone receptor.

Preferably said chimeric polypeptide consists of two modified growth hormone binding domains and one growth hormone binding domain of a growth hormone receptor.

Preferably said chimeric polypeptide consists of at least two modified site 2 growth hormone binding domains.

Aspects and embodiments which relate to a chimeric polypeptide comprising growth a hormone binding domain linked to a receptor binding domain are applicable to chimeric polypeptides comprising more than or a plurality of growth hormone binding domains. For example, vectors comprising nucleic acids encoding said chimeric polypeptides, pharmaceutical compositions comprising said polypeptides, cell-lines expressing said chimeric polypeptides, methods to manufacture said polypeptides and methods of treatment utilising said polypeptides are all within the scope of the invention with respect to this species of chimeric polypeptide.

An embodiment of the invention will now be described by example only and with reference to the following table and figures:

Table 1 represents a summary of the amino acid substitutions to site 1 and site 2 of human GH;

BRIEF DESCRIPTION OF THE DRAWINGS

FIG. 5. Sequence of the GH.G120R gene, showing the start codon, 6×His tag, relevant restriction sites, stop codons and the G120R mutation (CGC). The actual GH.G120R component is shown in CAPITALS, and the sequenced regions are shown in bold FIG. 6. Sequence of the 1A7 gene, showing the start codon, 6×His tag, relevant restriction sites, stop codons and the G120R mutation (CGC). The actual GH.G120R-$(G_4S)_4$-GHR(b) component is shown in CAPITALS, and the sequenced regions are shown in bold;

FIG. 7. Sequence of the 1B2 gene, showing the start codon, 6×His tag, relevant restriction sites, stop codons and the G120R mutation (CGC). The actual GH.G120R-$(G_4S)_4$-GHR(flec) component is shown in CAPITALS, and the sequenced regions are shown in bold;

FIG. 8. Sequence of the 1C3 gene, showing the start codon, 6×His tag, relevant restriction sites, stop codons and the G120R mutation (CGC). The actual GH.G120R-$(G_4S)_4$-GH.G120R component is shown in CAPITALS, and the sequenced regions are shown in bold;

FIG. 12 is the amino acid sequence of unmodified GH;

FIG. 13 is the nucleic acid sequence of unmodified GH.

MATERIALS AND METHODS

The methods to generate modified GH at site 1 and/or site 2 are disclosed in U.S. Pat. Nos. 5,849,535; 5,854,026; 6,004,931; 6,022,711; 6,057,292; and 6,136,563 each of which is incorporated by reference.

DNA Constructs

Generation of Site 2 Mutated GH Antagonist (GHa)

The cDNA for human GH (FIG. 1) has been PCR amplified from human pituitary tissue and cloned into the vector pTrcHis-Topo (pTrcHis-TOPO-GHstop). The GHR extracellular domain was amplified from human liver cDNA using PCR.

Growth Hormone Antagonist (G120R) Constructs

G120R Mutation of Growth Hormone

The growth hormone (GH) gene was mutated using the phagemid ssDNA mutation method. The GH gene was first sub-cloned from pTrcHisGH into pT7T318 between BamHI and HindIII sites, to produce pT7T318-GH. This plasmid was then transformed into *E. coli* CJ236 and single stranded ssDNA produced.

The ssDNA pT7T318-GH was then mutated by changing the codon for Gly120 from GGC to CGC, the primer GH.(G120R)For was used (Table 1).

Figure 1:
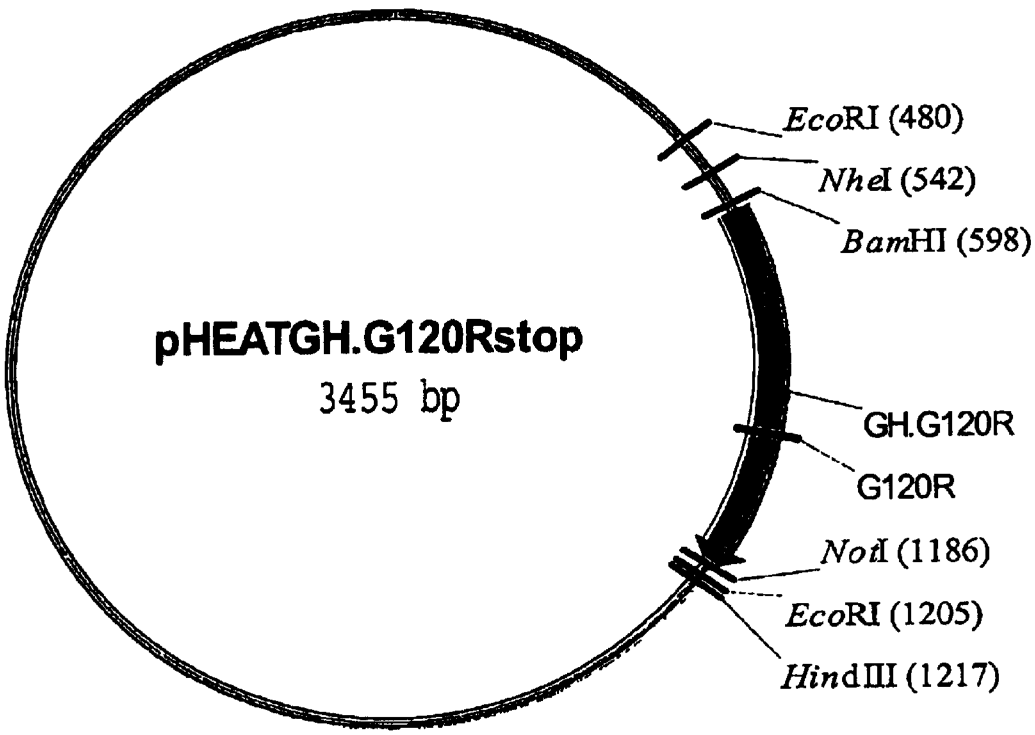
FIG. 1 Plasmid map of pHEAT.GH.G120R, which was generated by ligating the GH.G120R gene, synthesised by PCR, between the BamHI and NotI restriction sites. The selective marker on the plasmid is $Amp^R$.

The dsDNA pT7T318-GH.G120R produced after the mutation process was then used to sub-clone the GH.G120R into a pHEAT vector, this gave pHEAT.GH.G120R (FIG. 1).

Generation of GH.G120R Constructs

χ1A7 [GH.G120R-$(G_4S)_4$-GHR(b)]=GHa linked to b domain of GHR.

Figure 2:
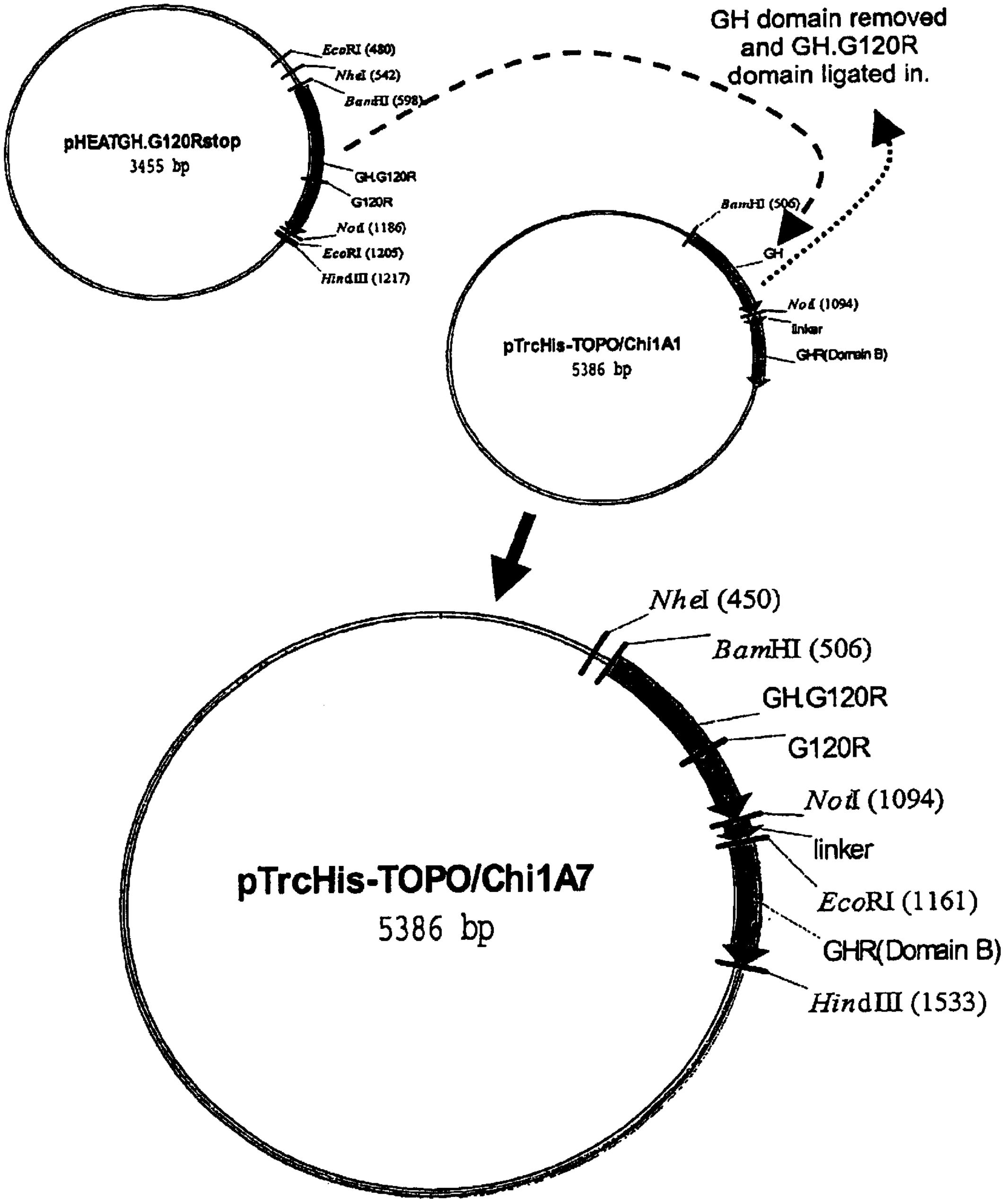
FIG. 2 Plasmid map of pTrcHis-TOPO. 1A7, which was generated by ligating the GH.G120R gene between the BamHI and NotI sites in pTrcHis 1A1. The linker is $(G_4S)_4$, and the selective marker on the plasmid is $Amp^R$.

The GH.G120R gene was excised from pHEAT.GH.G120R (FIG. 1) using the restriction sites BamHI and NotI. The gene was then ligated in place of the GH gene in pTrcHisχ1A1 [GH-$(G_4S)_4$-GHR(b)] (FIG. 2). The resulting plasmid was transformed into *Escherichia coli* XL1 Blue and plated on LB (0.3% glucose, 50 μg/ml ampicillin, 12.5 μg/ml tetracycline) agar plates.

χ1B2 [GH.G120R-$(G_4S)_4$-GHRflec]=GHa linked to full length extracellular domain of the GHR.

Figure 3:
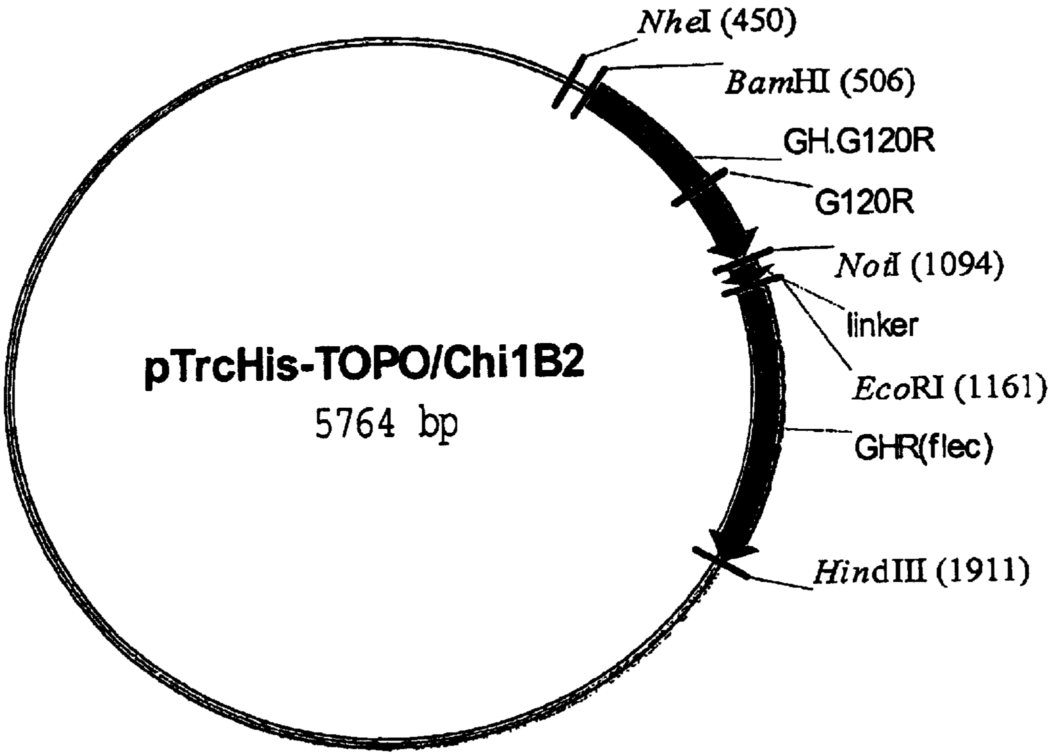
FIG. 3 Plasmid map of pTrcHis-TOPO. 1B2, which was generated by ligating the GH.G120R gene between the BamHI and NotI sites in pTrcHis 1B1. The linker is $(G_4S)_4$, and the selective marker on the plasmid is $Amp^R$.

The strategy used to generate the χ1A7 gene was repeated, however the recipient vector was pTrcHisχ1B1 [GH-$(G_4S)_4$-GHRflec] (FIG. 3). The resulting plasmid was transformed into *E. coli* XL1 Blue and plated on LB (0.3% glucose, 50 μg/ml ampicillin, 12.5 μg/ml tetracycline) agar plates.

χ1C3 [GH.G120R-$(G_4S)_4$-GH.G120R]=GHa tandem.

Figure 4:
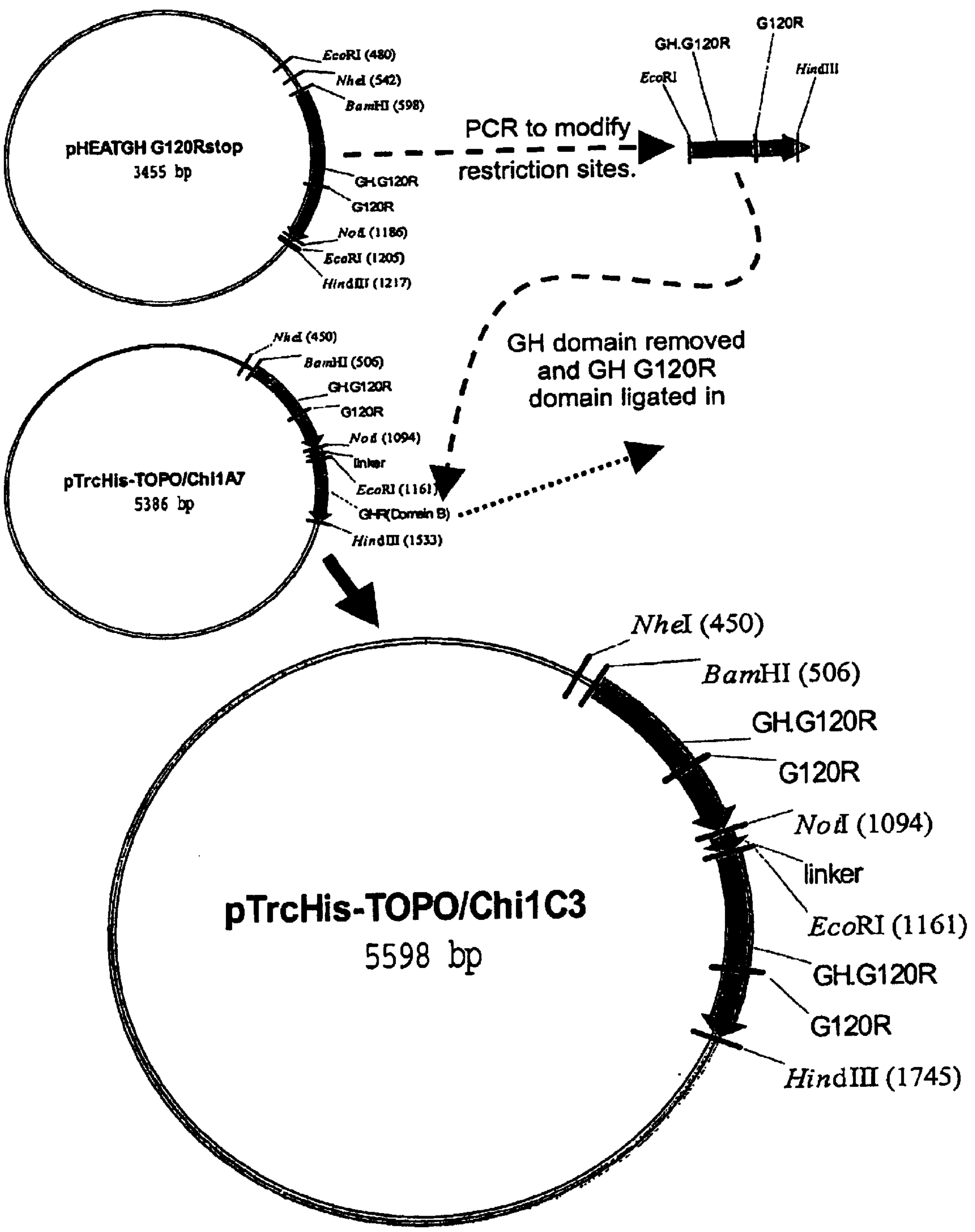
FIG. 4 Plasmid map of pTrcHis-TOPO. 1C3, which was generated by ligating the GH.G120R gene between the EcoRI and HinDIII sites in pTrcHis 1A7. The linker is $(G_4S)_4$, and the selective marker on the plasmid is $Amp^R$.

A PCR reaction was performed on pTrcHisGH using the primers DiGHEcoF1 and DiGHHinR1 (Table 1). The PCR product was then digested with EcoRI and HindIII, this was then ligated in place of the GHR(b) domain in pTrcHisχ1A1 [GH-$(G_4S)_4$-GHR(b)] (FIG. 4). The resulting plasmid was transformed into the recombinant deficient *E. coli* SURE and plated on LB (0.3% glucose, 50 μg/ml ampicillin, 12.5 μg/ml tetracycline, 50 μg/ml kanamycin) agar plates.

Sequencing Results

Plasmids containing the construct genes were sequenced. The sequences of the genes and the regions sequenced for GH.G120R, χ1A7, χ1B2 and χ1C3 are shown in FIGS. 5-8, respectively.

Expression Studies

Single colonies were used to inoculate 3 ml LB (0.3% glucose, 50 μg/ml ampicillin, 12.5 μg/ml tetracycline) broth for *E. coli* XL1 Blue cells and LB (0.3% glucose, 50 μg/ml ampicillin, 12.5 μg/ml tetracycline, 50 μg/ml kanamycin) broth for *E. coli* SURE cells. These were grown, shaking, overnight at 37° C.

4 mls of 4YT media, containing the appropriate antibiotics, were then inoculated with 200 μl of the overnight LB culture. These were grown for 3 hours, 1 ml samples were then taken ($T_0$ samples).

The 4YT cultures were then induced with IPTG to a final concentration of 1 mM and then further incubated for another 4 hours ($T_4$ samples).

The $T_0$ and $T_4$ samples were processed immediately after they had been taken. They were first centrifuged to pellet the cells, the supernatant was then discarded and the pellet processed for running on a SDS PAGE gel. Protein was visualised on these PAGE gels by either Coomassie staining or by western blot using an anti-GH primary antibody to probe for the construct.

Figure 9:
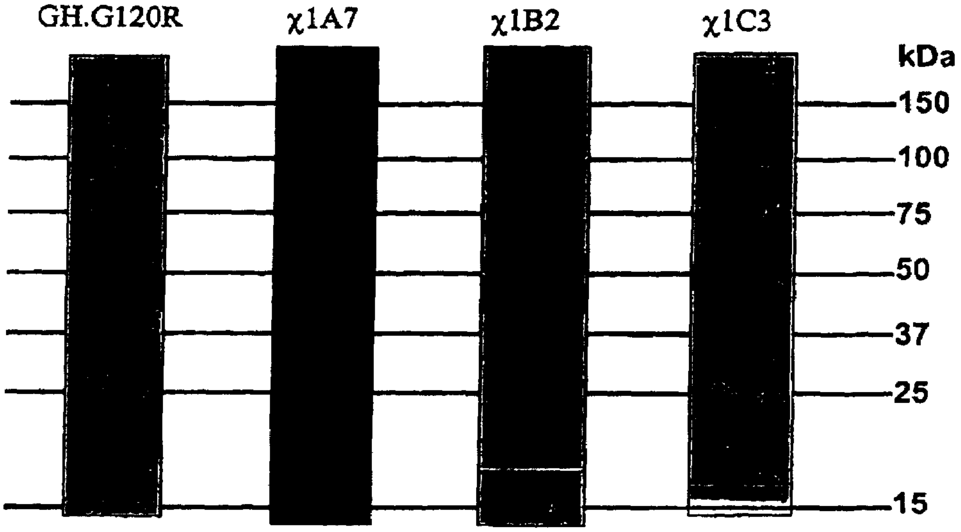
FIG. 9. Western blots using anti-human GH as the primary antibody of 15% SDS PAGE gels for the expression studies of GH.G120R, 1A7, 1B2 and 1C3. Expression was from the pTrcHis vector in *E. coli* XL1 Blue or *E. coli* SURE cells, these samples were taken 4 hours after induction with 1 mM (final concentration) IPTG. The blots show that GH.G120R and 1C3 produce single bands, while the samples of 1A7 and 1B2 contain cleavage products.

In all cases the Coomassie stained PAGE gels do not show over-expression of the construct. However, the constructs are observed on the western blots (FIG. 9). These show that in all cases protein of the correct size is expressed.

Purification

In general protein was purified from 4×250 ml cultures grown in 4YT, containing the appropriate antibiotics, and induced for 4-5 hours with IPTG to a final concentration of 1 mM. The cells were harvested by centrifugation and lysed by treatment with lysozyme and sodium deoxycholate followed by sonication.

The lysed cells were centrifuged to remove cell debris and the supernatant initially purified using Invitrogen ProBond Resin (Ni-column). Protein was eluted using 5 ml 0.5M imidazole.

The protein sample was further purified by diluting the eluant from the Ni-column 10 times in a suitable buffer and then passing it through a MonoQ ion-exchange column. Protein was eluted using a salt gradient of 0-1M NaCl over 20 ml at a rate of 0.5 ml/min; 0.5 ml fractions were collected. The fractions were then analysed for the presence of the construct, and the fractions containing the construct pooled.

Figure 10:
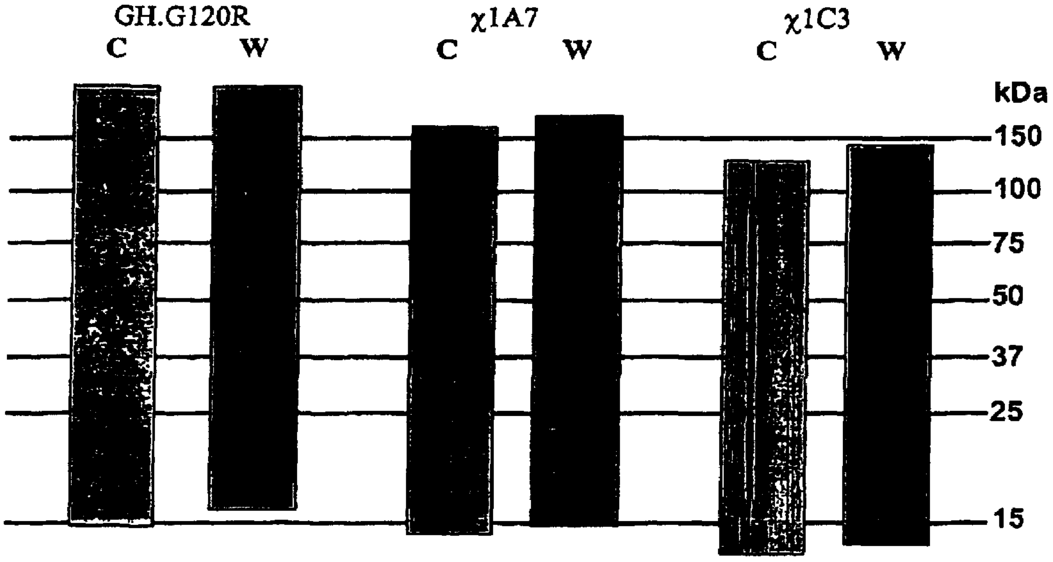
FIG. 10. Coomassie stained [C] 15% SDS PAGE gels of purified GH.G120R, 1A7 and 1C3. Western blots [W] of these samples using anti-human GH as the primary antibody are also shown. The coomassie stained gels show that the purified protein samples are >95% pure, however the western blots show that only GH.G120R and 1C3 produce single bands, while the sample of 1A7 contain cleavage products.

The purified protein was analysed by SDS PAGE (Coomassie staining and western blot) (FIG. 10) and assayed to measure its concentration. The protein was then submitted for the bioassay.

In the cases of χ1A7 and χ1B2, which showed cleaved products by western blot, the constructs were submitted to the Rapid Translation System (RTS) for in vitro transcription. Previous, studies on χ1A1 and χ1B1 have shown that cleavage was greatly reduced using the RTS system in conjunction with protease inhibitors and chaperones for expression.

Bioassay

The purified constructs were submitted to the Asterion standard GH bioassay. Prepared 293 Hi, which stably express growth hormone receptor, were stimulated with the construct using a range of doses. A second duplicate plate was also prepared, but 25 ng/ml GH was added 30 min. after adding the construct to observe the antagonistic capability of the construct.

Figure 11A:
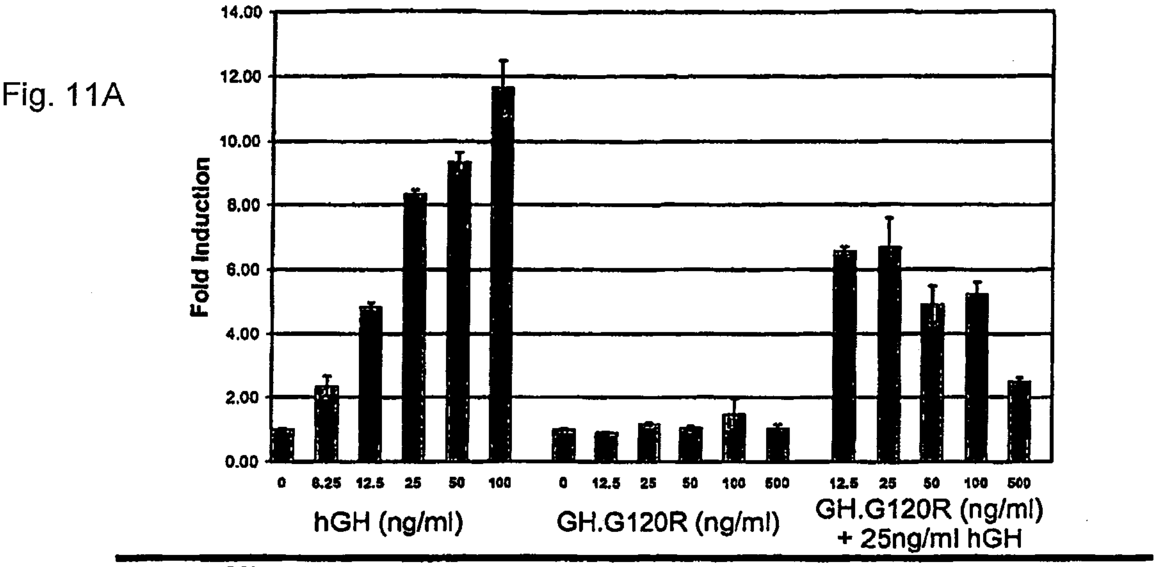
FIG. 11 A-C Graphs showing the results of the GH bioassay for GH.G120R (FIG. 11A), 1A7 (FIG. 11B) and 1C3 (FIG. 11C). Each graph shows a standard curve, the assay with the construct alone at different concentrations and the assay with the construct at different concentrations with 25 ng/ml hGH. These show that none of the proteins have inherent agonistic activity, but all have antagonistic activity with the GH.G120R being the most active, and 1A7 the least.
Figure 11B:
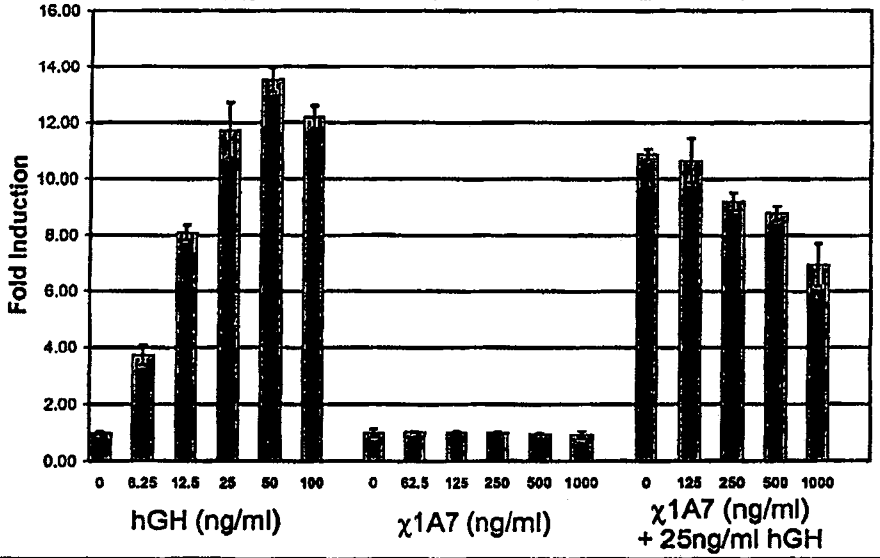
Figure 11C:
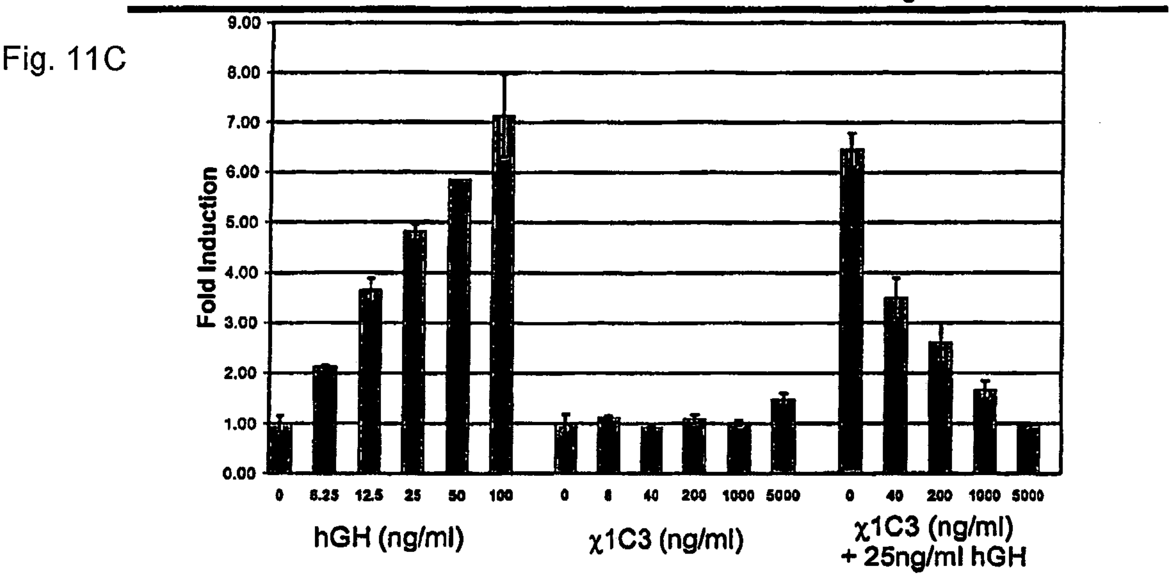

All the GH.G120R constructs had antagonistic activities (FIG. 11).

Screening of Antagonist Activity

An established bioassay is used to screen for antagonist activity (9). A permanent cell line expressing the full length GHR is transiently transfected with a luciferase reporter that binds activated Stat5 (9). Twenty-four hours later the cells are stimulated with GH for 6 hours with or without antagonist. The cells are then lysed and luciferase activity measured (9).

Testing Metabolic Clearance Rate in vivo

Sprague-Dawley rats are anaesthetised and cannulae implanted in femoral and jugular veins. Two days later GH chimera or tandem is administered by intravenous or subcutaneous injection. Blood samples are collected via the femoral cannula and chimera and tandem or oligomer protein levels measured by radio-immunoassay. Pharmacokinetic parameters are estimated using available computer programs fitting hormone concentration against time.

Table 1 represents a summary of amino acid substitutions made to site 1 of GH. Modifications to site 2 include the substitution of G120 for any of arginine; alanine; lysine; tryptophan; tyrosine; phenylalanine; or glutamic acid.

| H18 | H21 | Q22 | F25 | D26 | Q29 | E65 | R167 | K168 | D171 | K172 | E174 | I179 |
|---|---|---|---|---|---|---|---|---|---|---|---|---|
| D | N | | | | | | N | A | S | R | S | T |
| A | | A | A | A | A | A | | A | | | A | |
| A | | A | A | A | A | A | | | | | A | |
| D | | A | A | A | A | A | | A | | | S | |
| A | | A | A | A | A | A | | A | | | S | |
| D | | A | A | A | A | A | | A | | | A | |
| A | | A | A | A | A | A | | A | | | A | |
| D | N | | | | | | N | A | S | R | S | T |
| A | | A | A | A | A | A | | A | | | A | |

What is claimed is:

1. A fusion polypeptide comprising:

i) a modified binding domain of growth hormone wherein said modification is the substitution of amino acid residue glycine 120 in SEQ ID NO: 5; and ii) a growth hormone binding domain of growth hormone receptor wherein said polypeptide is an antagonist of growth hormone receptor.

2. A polypeptide according to claim 1 wherein the modification is a replacement of glycine with an amino acid selected from the group consisting of: arginine; alanine; lysine; tryptophan; tyrosine; phenylalanine; and glutamic acid.

3. A polypeptide according to claim 2 wherein said substitution is replacement of glycine 120 with arginine or lysine or alanine.

4. A polypeptide according to claim 1 wherein the growth hormone binding domain of growth hormone receptor is the extracellular domain of growth hormone receptor.

5. A polypeptide according to claim 4 wherein the extracellular domain of growth hormone receptor is the C-terminal SD-100 domain of growth hormone receptor.

6. A polypeptide according to claim 1 wherein, the modified binding domain of growth hormone is linked by a peptide linker to the growth hormone binding domain of growth hormone receptor.

7. A polypeptide according to claim 6 wherein the linker is a polypeptide which comprises 5 to 30 amino acid residues.

8. A polypeptide according to claim 7 wherein the linker comprises 10 to 20 amino acid residues.

9. A polypeptide according to claim 7 wherein the linker comprises at least one copy of the peptide Gly Gly Gly Gly Ser (SEQ ID NO:7).

10. A fusion polypeptide according to claim 1 wherein said modified binding domain of growth hormone comprises a substitution of: histidine 18 with aspartic acid, histidine 21 with asparagine, glycine 120 with arginine, arginine 167 with asparagine, lysine 168 with alanine, aspartic acid 171 with serine, lysine 172 with arginine, glutamic acid 174 with serine and isoleucine 179 with threonine.

11. A pharmaceutical composition comprising a polypeptide according to claim 1 and at least one pharmaceutical carrier or adjuvant.

12. A method of treating a condition selected from the group consisting of: giantism; acromegaly; cancer; diabetic retinopathy; diabetic nephropathy, diabetic complications and any disease of growth hormone excess, said method comprising administering to a patient in need thereof a pharmaceutically effective amount of a polypeptide according to claim 1.

13. A method according to claim 12 wherein said condition is acromegaly.

14. A method according to claim 12, wherein said patient is a mammal.

15. A method according to claim 14 wherein said condition is a cancer selected from the group consisting of: Wilm's tumour, osteogenic sarcoma, breast cancer, colon cancer, prostate cancer, and thyroid cancer.

16. A method of manufacturing a polypeptide according to claim 1, said method comprising:

i) providing a cell transformed or transfected with a vector comprising a nucleic acid molecule encoding said polypeptide;

ii) incubating said cell under conditions conducive to the production of said polypeptide; and iii) optionally isolating the polypeptide from the cell or a culture medium in which said cell is growing.

17. A method according to claim 16 wherein said polypeptide is provided with a secretion signal to facilitate the purification of the polypeptide from said cell.

18. A method according to claim 16 wherein said polypeptide is provided with an affinity tag to facilitate the purification of the polypeptide from said cell or the cell culture medium.

19. A nucleic acid molecule that encodes a fusion polypeptide according to claim 1.

20. A vector comprising the nucleic acid molecule according to claim 19.

21. A vector according to claim 20 wherein said vector is an expression vector adapted for recombinant expression.

22. A cell transformed or transfected with the vector according to claim 20.

23. A cell according to claim 22 wherein said cell is a eukaryotic cell selected from the group consisting of: a slime mold cell, a yeast cell, a mammalian cell, a plant cell and an insect cell.

24. A cell according to claim 22 wherein said cell is a prokaryotic cell.

25. A cell according to claim 22, wherein said cell is selected from the group consisting of Dictyostelium spp, Saccharomyces cerevisae, Pichia spp, Chinese Hamster Ovary, and Spodoptera spp.

* * * * *